(12) United States Patent
Berim

(10) Patent No.: US 11,660,077 B2
(45) Date of Patent: May 30, 2023

(54) SPECIMEN CONTAINER HOLDING APPARATUS

(71) Applicant: Ilya Berim, Princeton, NJ (US)

(72) Inventor: Ilya Berim, Princeton, NJ (US)

(*) Notice: Subject to any disclaimer, the term of this patent is extended or adjusted under 35 U.S.C. 154(b) by 896 days.

(21) Appl. No.: 16/588,437

(22) Filed: Sep. 30, 2019

(65) Prior Publication Data

US 2020/0107712 A1    Apr. 9, 2020

Related U.S. Application Data

(60) Provisional application No. 62/738,729, filed on Sep. 28, 2018.

(51) Int. Cl.
| | | |
|---|---|---|
| *B01L 9/00* | (2006.01) | |
| *A61B 10/00* | (2006.01) | |
| *A61B 1/267* | (2006.01) | |
| *B01L 3/00* | (2006.01) | |
| *A61B 1/00* | (2006.01) | |

(52) U.S. Cl.
CPC ...... *A61B 10/0045* (2013.01); *A61B 1/00147* (2013.01); *A61B 1/2676* (2013.01); *B01L 3/00* (2013.01); *B01L 3/502* (2013.01); *B01L 9/52* (2013.01); *B01L 3/50* (2013.01); *B01L 3/50825* (2013.01)

(58) Field of Classification Search
CPC .......................................... B01L 9/54
See application file for complete search history.

(56) References Cited

U.S. PATENT DOCUMENTS

| | | | |
|---|---|---|---|
| 2,627,857 A | | 2/1953 | Marcelli |
| 2,677,372 A | | 5/1954 | Barnish, Jr. |
| 2,761,558 A | * | 9/1956 | Mclean, Jr. ............ G02B 21/34 206/561 |
| 3,318,458 A | * | 5/1967 | Rothberg .................. B01L 9/52 34/239 |
| 3,615,257 A | * | 10/1971 | Frost ........................ B01L 9/52 422/534 |
| 3,833,030 A | | 9/1974 | Waldbauer, Jr. et al. |
| 3,853,158 A | | 12/1974 | Whitty |
| 3,930,928 A | | 1/1976 | Tapert |
| 5,169,603 A | * | 12/1992 | Landsberger ............ B01L 9/06 211/74 |
| 9,706,865 B2 | | 7/2017 | Shen |
| 9,840,179 B2 | | 12/2017 | Sawada et al. |
| 2002/0072714 A1 | | 6/2002 | Epstein et al. |

(Continued)

OTHER PUBLICATIONS

International Search Report and Written Opinion dated Apr. 8, 2020 for PCT/US2019/053864.

(Continued)

*Primary Examiner* — Paul S Hyun
(74) *Attorney, Agent, or Firm* — Suiter Swantz pc llo (57) ABSTRACT

A specimen container holding apparatus is disclosed. The apparatus is configured to hold a container for receiving liquids from a bronchoscope. The apparatus includes a needle guide with a first and a second opening configured to receive a needle of the bronchoscope. The first and second opening may be disposed on a removable tip of the needle guide. The removable tip may be detachably connected to a removable tip connection point. The apparatus may further include a slide holder configured to hold a slide.

17 Claims, 11 Drawing Sheets

(56) References Cited

U.S. PATENT DOCUMENTS

| | | |
|---|---|---|
| 2003/0196722 A1 | 10/2003 | Spero et al. |
| 2007/0276358 A1 | 11/2007 | Barzell et al. |
| 2008/0065024 A1 | 3/2008 | Witte |
| 2011/0144614 A1 | 6/2011 | Hereford |
| 2011/0253251 A1 | 10/2011 | Mudd |
| 2013/0084599 A1 | 4/2013 | Morimoto |
| 2014/0102579 A1 | 4/2014 | Mudd |
| 2017/0266393 A1 | 9/2017 | Tsukamoto |

OTHER PUBLICATIONS

CIVCO Medical Solutions, Safe. Efficient. Guiding Patient Care.—CIVCO Medical Solutions, 2011, www.civco.com, 6 pages.

* cited by examiner

SPECIMEN CONTAINER HOLDING APPARATUS

CROSS-REFERENCE TO RELATED APPLICATION

The present application claims the benefit under 35 U.S.C. § 119(e) of U.S. Provisional Application Ser. No. 62/738,729, filed Sep. 28, 2018, entitled BRONCHOSCOPIC ACCESSORIES AND MEDICAL DEVICES, naming Ilya Berim as inventor, which is incorporated herein by reference in the entirety.

TECHNICAL FIELD

The present invention generally relates to bronchoscopy, and more particularly to a specimen container holding apparatus equipped with a needle guide for guiding a needle, such as a bronchoscopy needle, toward the specimen container.

BACKGROUND

Bronchoscopy is an endoscopic technique of visualizing the inside of the airways for diagnostic and therapeutic purposes. A bronchoscope typically has a flexible cable housing a needle and/or cutter. When bronchoscopy is performed, sample tissue taken from a patient may be transferred to a specimen container or a slide for further medical analysis. Due to the flexibility of the bronchoscope cable, this requires two practitioners (e.g., one practitioner to hold the bronchoscope and the other practitioner to hold the specimen container and the cable) to perform the procedure and collect the sample from the patient. Such an approach is cumbersome and inefficient. Therefore, it would be advantageous to provide a system and method that cure one or more of the shortfalls of the previous approaches identified above.

SUMMARY

A specimen container apparatus is disclosed in accordance with one or more embodiments of the present disclosure. In one illustrative embodiment, the apparatus includes a container holder with a first plate, where the first plate includes a container receiver opening defined by an inner surface of the container holder configured to receive a specimen container. In another illustrative embodiment, the apparatus includes a needle guide. The needle guide is configured to receive a needle from a bronchoscope (or other medical device) through a first and a second opening on the needle guide, in order to drain a liquid from the bronchoscope to the specimen container.

A slide holder apparatus is disclosed in accordance with one or more embodiments of the present disclosure. In one illustrative embodiment, the slide holder includes a first plate with one or more depressions configured to receive a slide. In another illustrative embodiment, the apparatus includes a needle guide. The needle guide is configured to receive a needle from a bronchoscope through a first and a second opening on the needle guide, in order to drain a liquid from the bronchoscope to the specimen container.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1A-6, a specimen container holding apparatus equipped with a needle guide is disclosed, in accordance with one or more embodiments of the present disclosure.

Embodiments of the present disclosure are directed to a specimen container holder including a needle guide. In some embodiments, the needle guide includes a first and a second opening configured to receive a needle of a medical device (e.g., bronchoscope). In this regard, the needle guide may be used to hold the needle, allowing a user to drain a liquid from the bronchoscope. The needle guide may be used with the container holder and/or a slide holder (or by itself). The apparatus may be configured to receive a specimen container (e.g., bottle or jar) by a container receiver opening defined by an inner surface of the container holder. The apparatus may be configured to receive a slide by a depression on the slide holder.

Additional embodiments of the present disclosure are directed to an apparatus including a plurality of plates (e.g., a first plate and a second plate) attached by a plurality of supports. The plurality of plates may be detachably connected by the plurality of supports. In this regard, the plurality of plates and the plurality of supports may be disassembled and cleaned between uses. Alternatively, the plurality of plates may be permanently fixed by the plurality of supports.

Additional embodiments of the present disclosure are directed to an apparatus configured to receive a plurality of specimen containers. The apparatus may be configured to receive the plurality of specimen containers by a plurality of container receiver openings disposed on the first plate. The container receiver openings may be defined by a plurality of inner surfaces of the first plate. Alternatively, the apparatus may be configured to receive the plurality of specimen containers by having a container holder detachably connected to an additional container holder. In this regard, the detachably attachable additional container holder may allow for selective configuration of the number of specimen containers able to be housed on the apparatus.

Additional embodiments of the present disclosure are directed to an apparatus including a slide holder. The slide holder may include one or more depressions configured to receive one or more slides (e.g., microscope slides). The slide holder may be disposed on a first plate of the apparatus that includes one or more needle guides.

Additional embodiments of the present disclosure are directed to an apparatus including both a slide holder and a container holder. The apparatus may include a first plate which includes both of the slide holder and the container holder. Alternatively, the apparatus may include a slide holder detachably connected to the container holder.

Figure 1A:
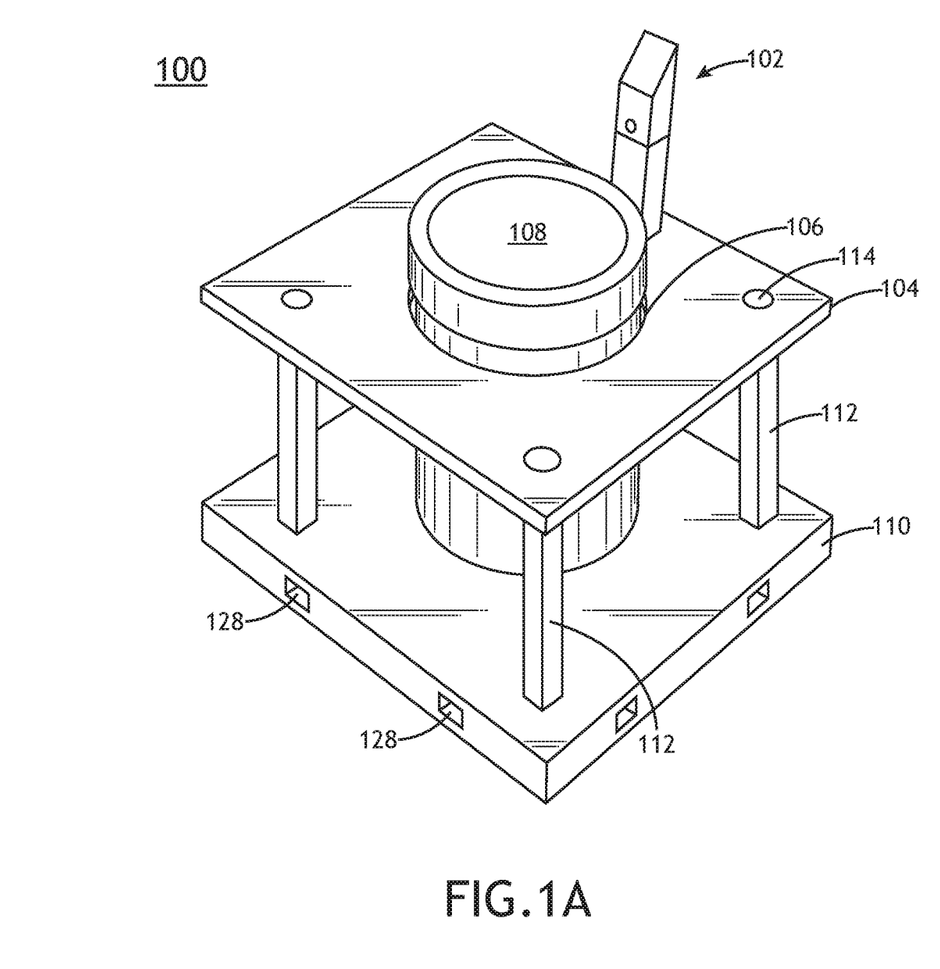
FIG. 1A illustrates an isometric view of a container holder, in accordance with one or more embodiments of the present disclosure.

FIG. 1A illustrates an isometric view of a container holder 100 including a needle guide 102, in accordance with one or more embodiments of the present disclosure. In some embodiments, the container holder 100 may include a first plate 104 with a container receiver opening defined by an inner surface 106, where the container receiver opening is configured to receive a specimen container 108. The inner surface 106 may be of suitable size and geometry such that the inner surface 106 may encompass the specimen container 108 (e.g., by a clearance or interference fit between the inner surface 106 and the specimen container 108). In this regard, container receiver opening may be defined by one of a circular hole, an oval shaped hole, a square hole, or any other suitable hole for receiving the specimen container. Furthermore, the inner surface 106 may include features such as, but not limited to, a flange (e.g., a lip or a ridge), a chamfered edge, or any other feature suitable for receiving and/or retaining the specimen container 108.

In some embodiments, the container holder 100 includes a second plate 110 and a plurality of supports 112, where the second plate 110 is disposed below the first plate 104, and where the plurality of supports 112 are disposed between and connecting the first plate 104 and the second plate 110. The first plate 104 may be fixed to the second plate 110 by the plurality of supports 112 (e.g., by adhesive, plastic welding, etc.). Alternatively, the first plate 104 may be detachably connected to the second plate 110 by the plurality of supports 112 (e.g., by an interference fit). The ability to detachably connect the first plate 104 and the second plate 110 may allow for ease of cleaning. As depicted in FIG. 1A, the first plate 104 and the second plate 110 may include holes 114 for the supports 112.

Figure 1B:
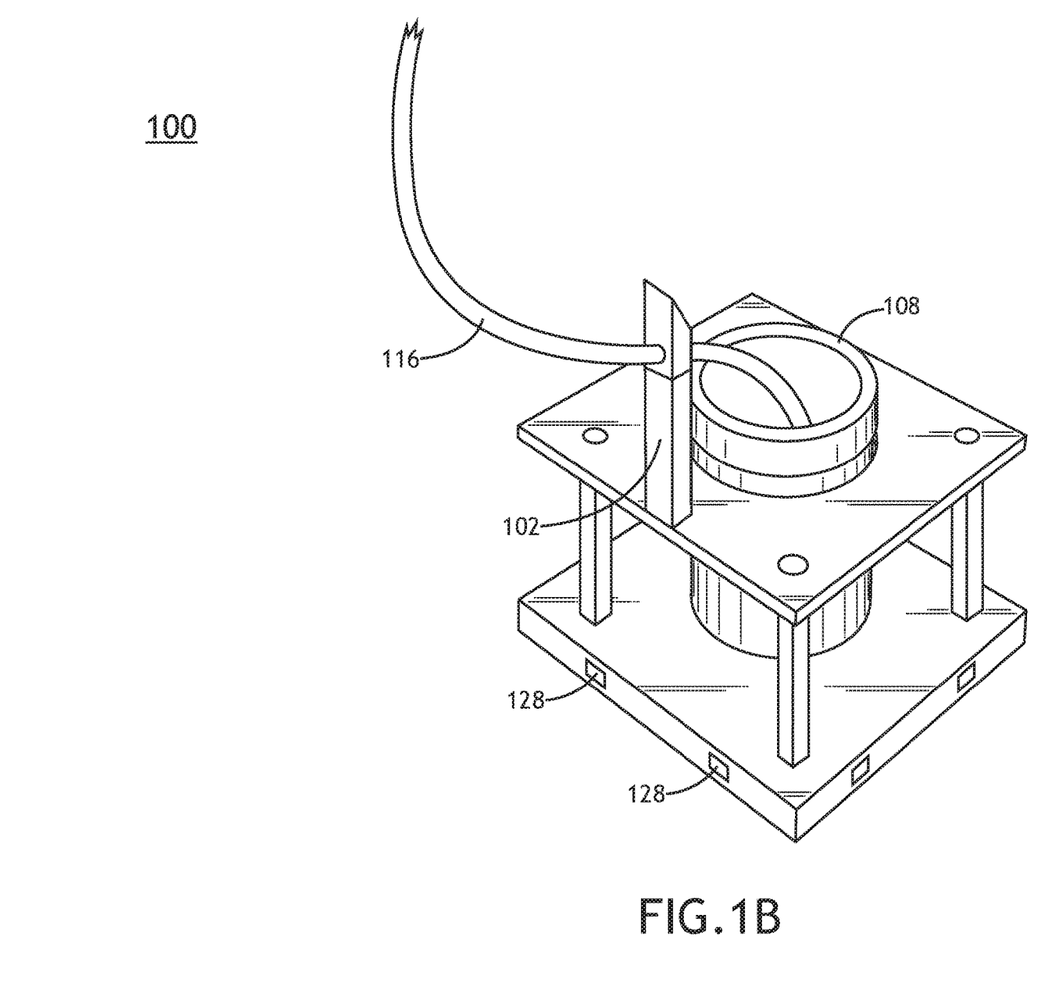
FIG. 1B illustrates an isometric view of a container holder, in accordance with one or more embodiments of the present disclosure.

FIG. 1B depicts the needle guide 102 receiving a needle 116 of a bronchoscope, in accordance with one or more embodiments of the present disclosure.

In some embodiments, the needle guide 102 may be configured to receive at least a portion of a bronchoscope (e.g., a needle 116 or a catheter), for draining fluid from the bronchoscope through the needle to a specimen container 108 held by the container holder 100 and/or a slide held by a slide holder. It is envisioned that the use of the needle guide 102 may reduce the dexterity required to operate the bronchoscope and/or reduce a likelihood of spilling while draining to the specimen container 108 or a slide.

Figure 1C:
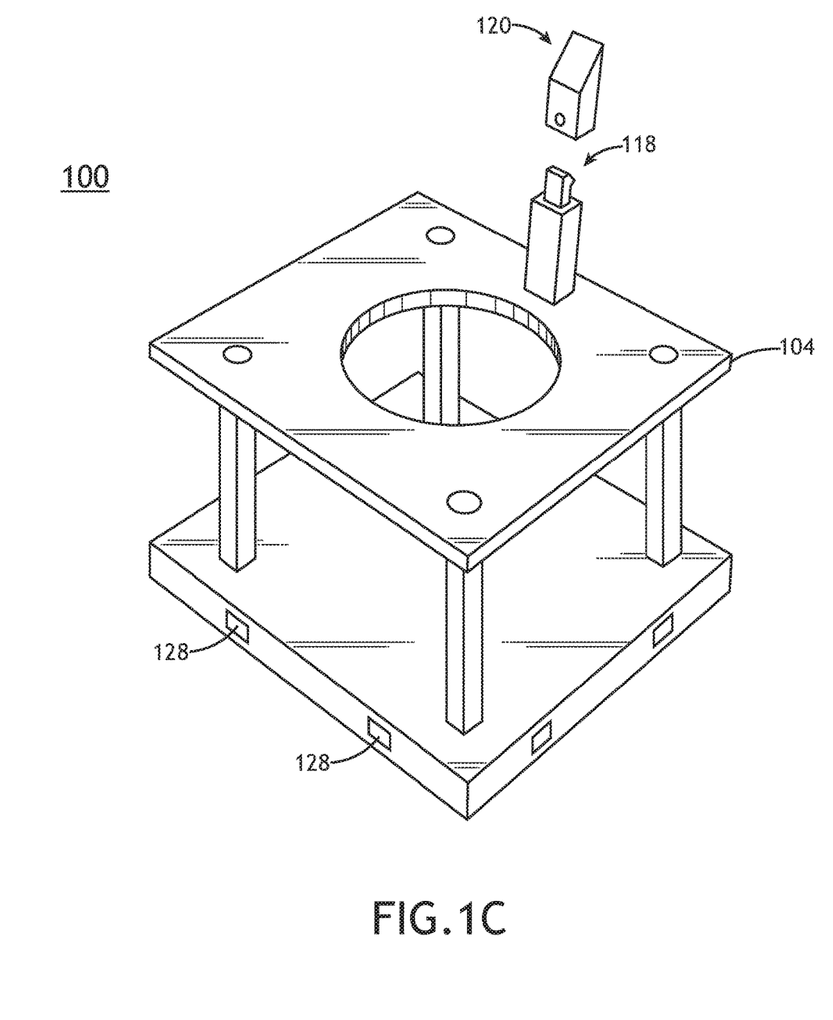
FIG. 1C illustrates an isometric view of a container holder, in accordance with one or more embodiments of the present disclosure.

FIG. 1C depicts the container holder 100 with the needle guide 102 where a removable tip 120 is detached from a removable tip attachment point 118, in accordance with one or more embodiments of the present disclosure.

In some embodiments, the container holder 100 includes needle guide 102 with a removable tip 120. The removable tip 120 may be detachably connected to a removable tip attachment point 118. The removable tip 120 may be detachably connected to the removable tip attachment point 118 by one or more means, including, but not limited to, a clip (e.g., C-clips), a threaded fastener, an interference fit, or a retaining pin (e.g., split pin, circle cotter, cotter pin). The removable tip attachment point 118 may be attached to a variety of components of the container holder 100 including, but not limited to, the first plate 104. The removable tip attachment point 118 may be attached to said components by a variety of means, including, but not limited to, adhesive, plastic welding, thread, or formed during manufacturing (e.g., injection molded). Furthermore, the removable tip attachment point 118 may be housed in a slot (not depicted), in accordance with one or more embodiments of the present disclosure.

Figure 1D:
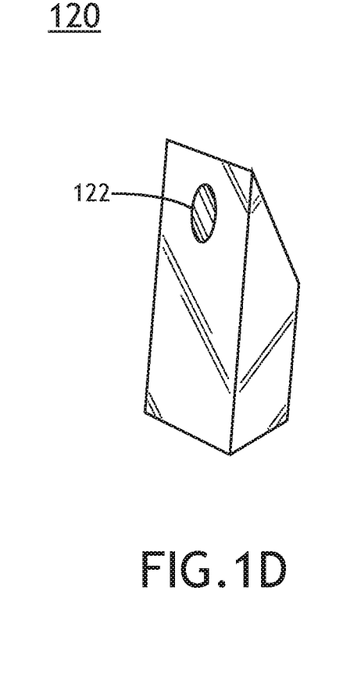
FIG. 1D illustrates an isometric view of a removable tip of a needle guide, in accordance with one or more embodiments of the present disclosure.
Figure 1E:
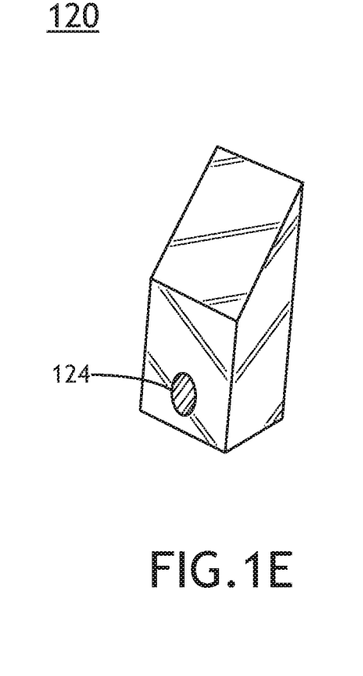
FIG. 1E illustrates an isometric view of a removable tip of a needle guide, in accordance with one or more embodiments of the present disclosure.

FIGS. 1D-1E depicts removable tip 120, in accordance with one or more embodiments of the present disclosure. In some embodiments, the needle guide 102 may include a first opening 122 and a second opening 124. The first opening 122 may have a first diameter and the second opening 124 may have a second diameter, where the first diameter is larger than the second diameter. The first opening 122 may generally be shaped with an opening suitable for easily receiving components of a bronchoscopy device (e.g., the needle 116). In this regard, the first opening 122 may be larger than said component, allowing for ease-of-insertion of said component. The second opening 124 may be generally a similar size as the inserted components of the bronchoscopy device (e.g., the needle 116). In this regard, the components may be secured by the second opening 124 such that the second opening 124 may constrain the needle 116 after the needle 116 is received through the first opening 122 and second opening 124. Receiving the needle 116 through the needle guide 102 may be beneficial in retaining the needle by the container holder 100, thus assisting with draining a liquid from the needle to the specimen container 108.

Figure 1F:
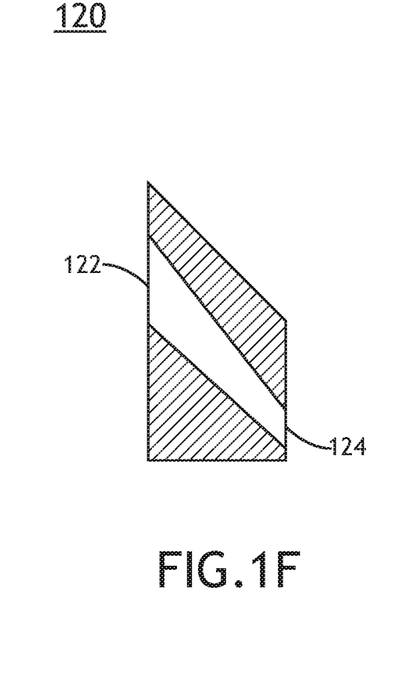
FIG. 1F illustrates a cross section view a removable tip of a needle guide, in accordance with one or more embodiments of the present disclosure.

FIG. 1F depicts a cross sectional view of the removable tip 120, in accordance with one or more embodiments of the present disclosure. In some embodiments, the needle guide 102 includes a removable tip attachment point 118 and a removable tip 120. The removable tip 120 may include the first opening 122 and the second opening 124. As depicted in FIGS. 1D-1E, the first opening 122 may taper towards the second opening 124. It is envisioned that the taper may be pre-formed (e.g., during an injection molding process) or formed during post-processing. The first opening 122 may be disposed on a side face of the removable tip 120 and the second opening 124 may be disposed on a second side face of the removable tip 120. The first opening 122 may be disposed one the removable tip 120 at a location above the second opening 124. In this regard, a needle inserted through the first opening 122 to the second opening 124 may be situated at a downward angle. Such downward angle may assist in retaining the needle in the needle guide 102.

Although the first opening 122 and the second opening 124 are described in relation to the removable tip 120, this is not intended as a limitation on the scope of present disclosure. For example, the needle guide 102 may include a nonremovable tip, which includes both the first opening 122 and the second opening 124. However, the use of removable tip 120 may assist in cleaning of the apparatus. In this regard, a used removable tip may be removed from the apparatus and replaced with a new removable tip.

The configuration of the removable tip in FIGS. 1D-1F may depict a slanted top surface of the removable tip 120. It is noted that such a feature is not intended as a limitation on the scope of the present disclosure. For example, a top surface of the removable tip 120 may be some geometry other than slanted (e.g., flat, curved, etc.). Furthermore, either one of the first opening 122 or the second opening 124 may be disposed on the top surface. In particular, some configurations may improve ease-of-manufacturing, ease-of-insertion, and/or ability to retain the needle.

Figure 1G:
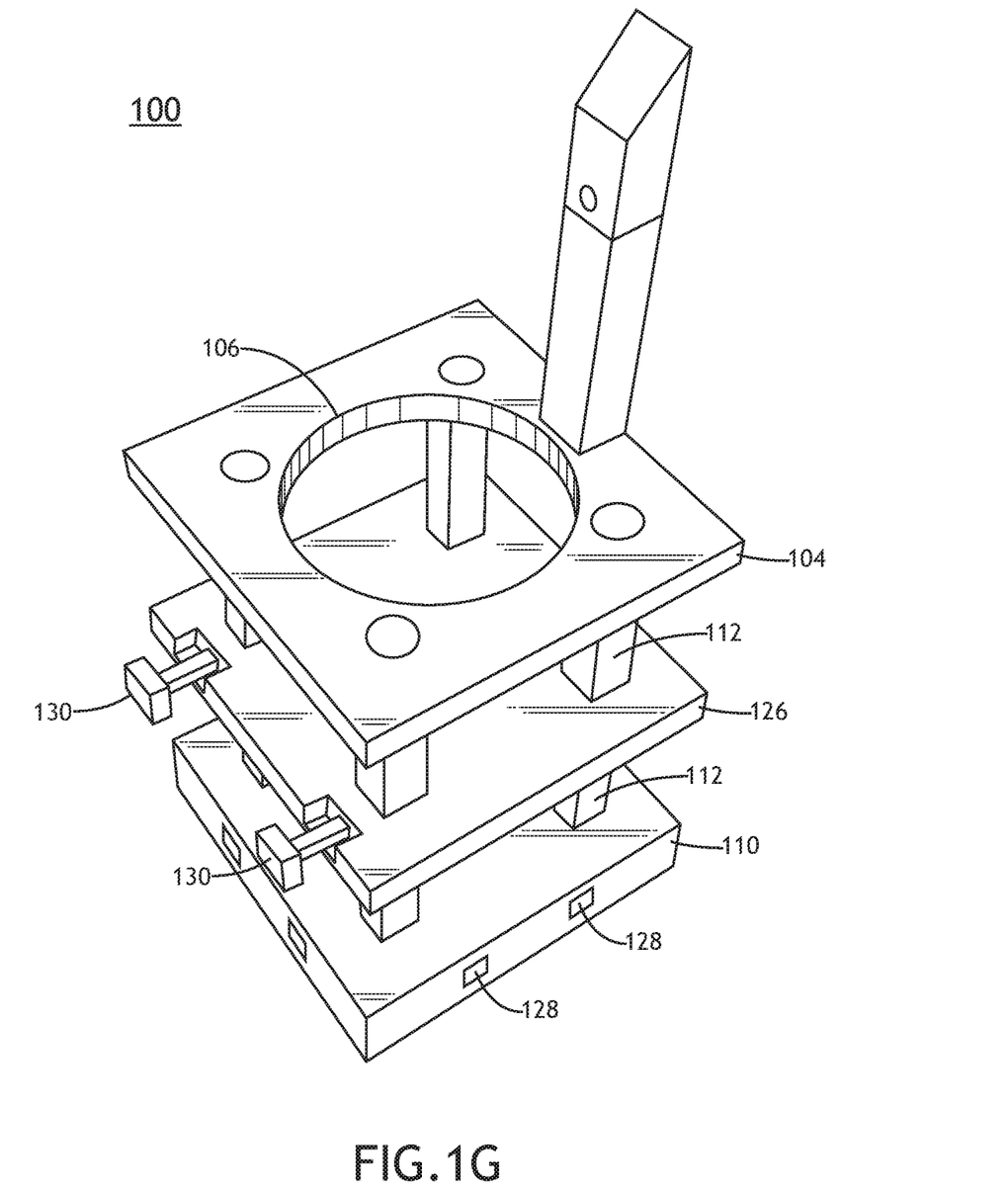
FIG. 1G illustrates a container holder including a needle guide, in accordance with one or more embodiments of the present disclosure.

FIG. 1G depicts a container holder 100 including one or more intermediate plates 126 disposed between the first plate 104 and the second plate 110, in accordance with one or more embodiments of the present disclosure. In some embodiments, the container holder 100 includes one or more intermediate plates 126 disposed between the first plate 104 and the second plate 110. The intermediate plates 126 may be attached to the first and the second plates 104,110 by the plurality of supports 112. As depicted in FIG. 1G, the first plate 104 may include the container receiver opening defined by an inner surface 106, where the container receiver opening is configured to receive a specimen container. In this configuration, the intermediate plate 126 may act as a base for the specimen container received by the inner surface 106. Alternatively, the intermediate plate 126 may include an inner surface (not depicted), such that both the intermediate plate 126 and the first plate 104 may be configured to receive a specimen container. In this regard, the intermediate plate 126 may provide additional lateral constraint for the specimen container. Although the intermediate plate 126 is described in regard to the container holder 100, this is not intended as a limitation on the present disclosure. For example, the intermediate plate 126 may be used with a slide holder including a first plate and a second plate.

Figure 2A:
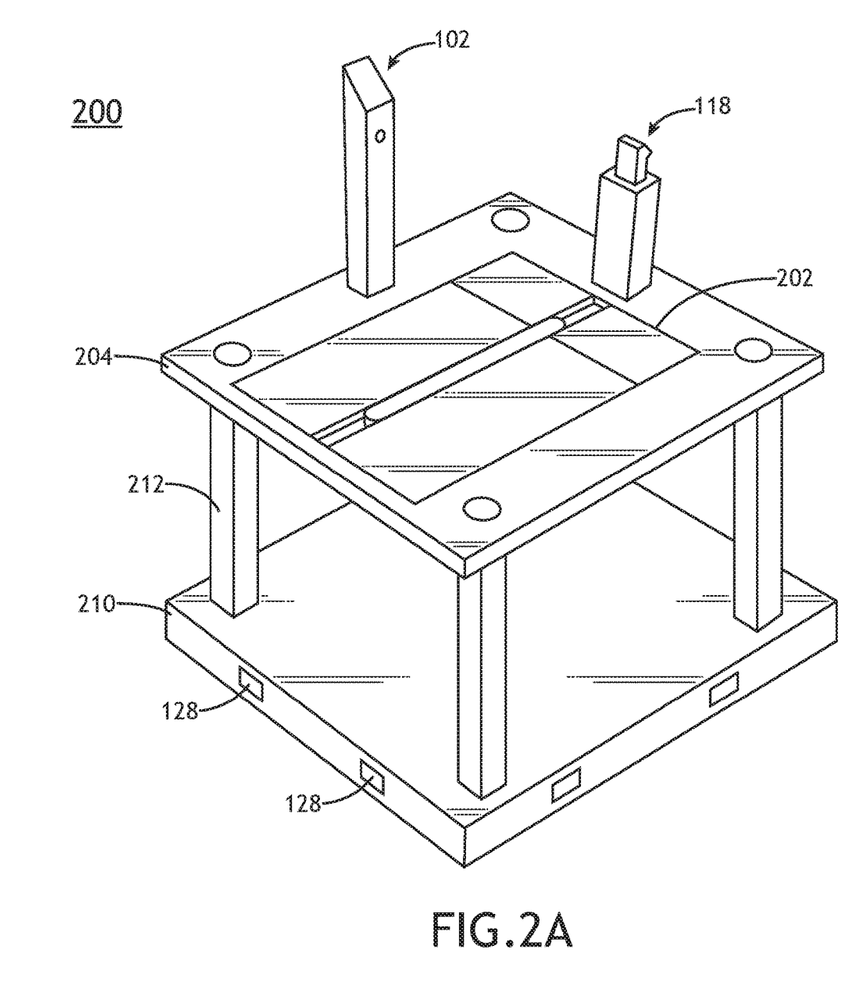
FIG. 2A illustrates an isometric view of a slide holder, in accordance with one or more embodiments of the present disclosure.

FIG. 2A depicts the slide holder 200 with needle guide 102, in accordance with one or more embodiments of the present disclosure. In some embodiments, a slide holder 200 may be disposed on a first plate 204, where the first plate 204 includes one or more depressions 202. The depressions 202 may be offset from a top face of the first plate 204. In this regard, the depressions 202 may be of suitable size and geometry such that a slide (e.g., a microscope slide) may fit within the depressions 202 (e.g., by a clearance or interference fit). Furthermore, the first plate 204 may include features such as, but not limited to, a flange (e.g., a lip or a ridge), a chamfered edge, spring/stage clips, or any other feature suitable for receiving and/or retaining the one or more slides.

In some embodiments, the first plate 204 of the slide holder 200 may include one or more needle guides 102. The one or more needle guides 102 may be attached in any suitable manner, in accordance with one or more embodiments of the present disclosure. Furthermore, the needle guides 102 may be disposed on the first plate 204 in a variety of configurations, such as, but not limited to, at a side of the depression 202 or at an end of the depression 202. The number and configuration of needle guides 102 and depressions 202 may vary by use case. Furthermore, the needle guide 102 may be attached to a slot (not depicted) on the first plate 204, in accordance with one or more embodiments of the present disclosure. The dimensions of the depressions 202 are not intended to be limiting on the scope of the present disclosure. For example, a depression may be of any suitable dimension for receiving and retaining a slide.

In some embodiments, the slide holder 200 includes a second plate 210 and a plurality of supports 212, where the second plate is disposed below the first plate 204, and where the supports 212 are disposed between the first plate 204 and the second plate 210. It is noted that the discussion related to supports 112 provided above should be interpreted to extended to supports 212. Furthermore, the second plate 210 may include features similar to the first plate 204 such as, but not limited to, depressions 202 and needle guides 102. In this regard, stacking the first plate 204 on top of the second plate 210 may allow for additional slides to be held by the slide holder 200.

Figure 2B:
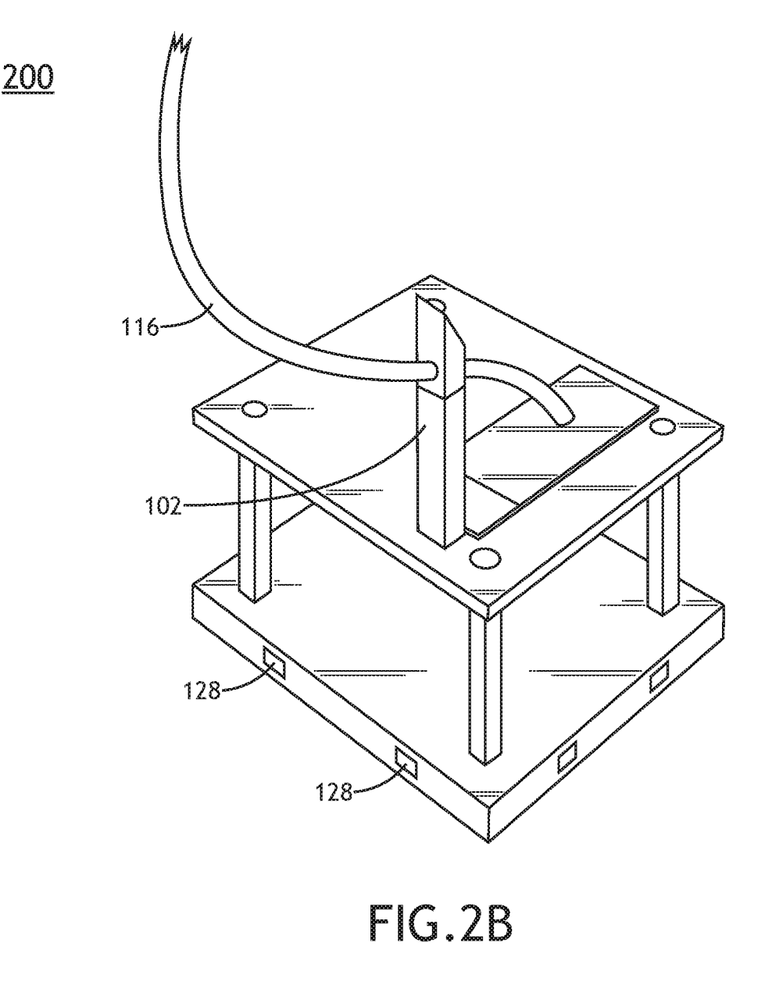
FIG. 2B illustrates an isometric view of a slide holder, in accordance with one or more embodiments of the present disclosure.

FIG. 2B depicts the needle guide 102 of the slide holder 200 receiving the needle 116 of the bronchoscope, in accordance with one or more embodiments of the present disclosure. As discussed previously herein, the needle guide 102 of the slide holder 200 may receive the needle 116 through the first opening 122 and the second opening 124. Similar to the benefits of receiving the needle 116 for container holder 100, receiving the needle 116 for slide holder 200 may assist with draining a liquid from the needle 116 to the slide.

Figure 3:
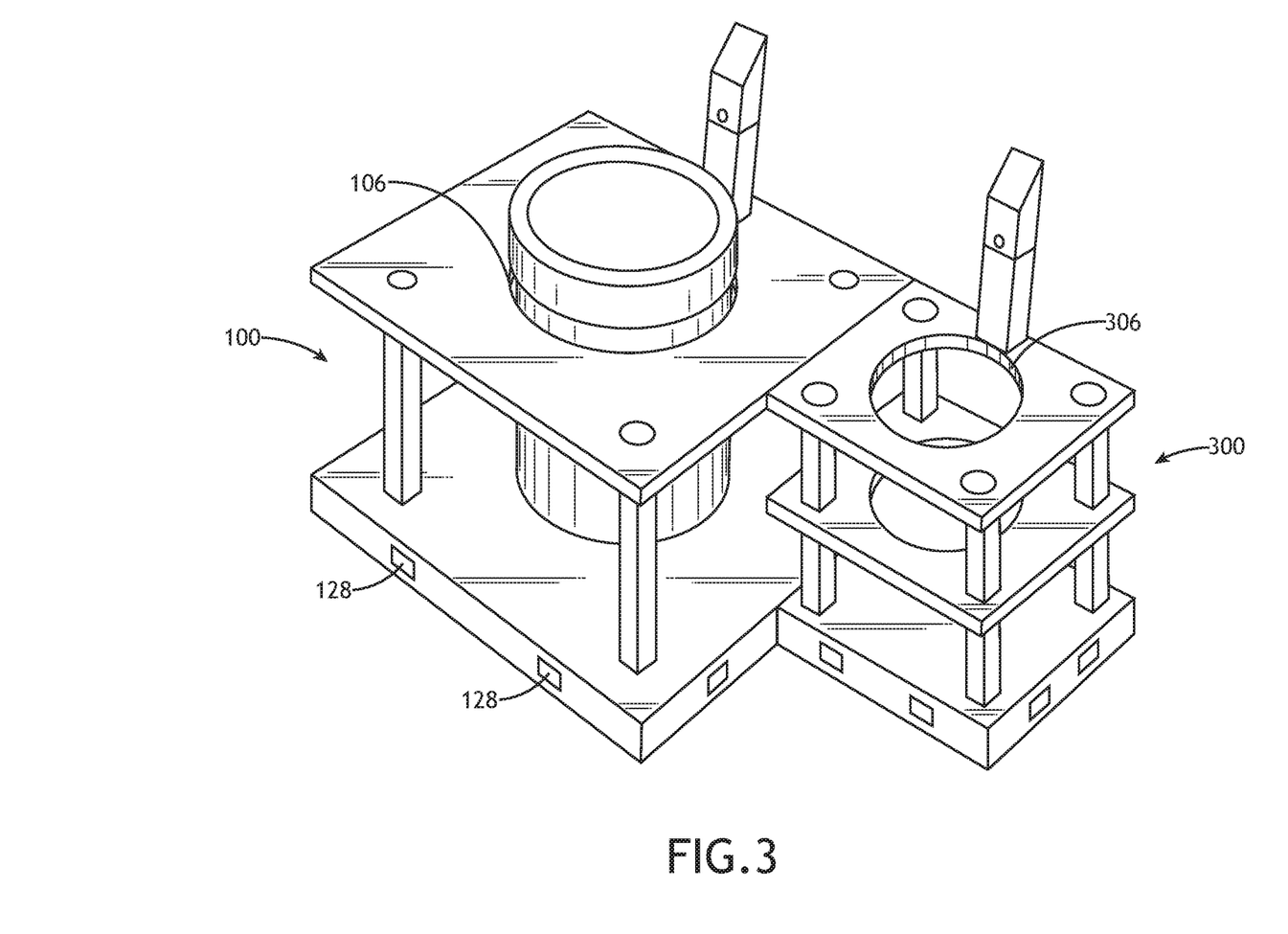
FIG. 3 illustrates an isometric view of a container holder detachably connected to another container holder, in accordance with one or more embodiments of the present disclosure.

FIG. 3 depicts container holder 100 detachably connected to an additional container holder 300, in accordance with one or more embodiments of the present disclosure. In some embodiments, container holder 100 may be detachably connected to an additional container holder 300. The additional container holder 300 may include an additional container receiver opening defined by inner surface 306, where the additional container receiver opening is suitable for receiving a specimen container. The container holders 100, 300 may be configured to detachably attach by any suitable means, including, but not limited to, dowels, clips, or sliding pins connected to the first and second plates 104, 110 of the container holder 100. In this regard, the first and second plates 104, 110 may include one or more openings (e.g., square openings 128 as depicted in FIG. 1A), which may be configured to receive a dowel or sliding pin. It is to be understood that the one or more openings may be any suitable geometry, including, but not limited to, square, circular, or oval. The ability to detachably connect container holders and/or slide holders may allow for selective customization of the number of specimen containers and/or slide holders able to be held. In this regard any number of container holders and/or slide holders may be detachably connected together.

In some embodiments, a sliding pin is used to connect a container holder to an additional container holder. FIG. 1G depicts sliding pins 130 received by the intermediate plate 126. The sliding pins 130 may be slid through square opening 128 (e.g., a square opening disposed on the first plate 104 or the second plate 110) to a second square opening (not depicted) of the additional container holder.

As depicted in FIG. 3, the additional container holder 300 includes inner surface 306. In this embodiment, the additional container holder 300 is detachably connected to the container holder 100. It is noted that the additional portion attached to the container holder 100 is not limited to the additional container holder 300. For example, a slide holder (e.g., slide holder 200) may be configured to detachably connect to the container holder 100. By way of another example, the first plate 204 and/or the second plate 210 of the slide holder may be configured to detachably connect by any suitable means, including, but not limited to, dowels, clips, or sliding pins. In this regard, the discussion pursuant to the detachably connectable container holders may also be understood as applying to detachably container a container holder to a slide holder. Similarly, a plurality of slide holders (e.g., slide holders 200) may be configured to attach to one another. In this regard, any number of containers holders and/or slide holders may be detachably connected together.

Figure 4:
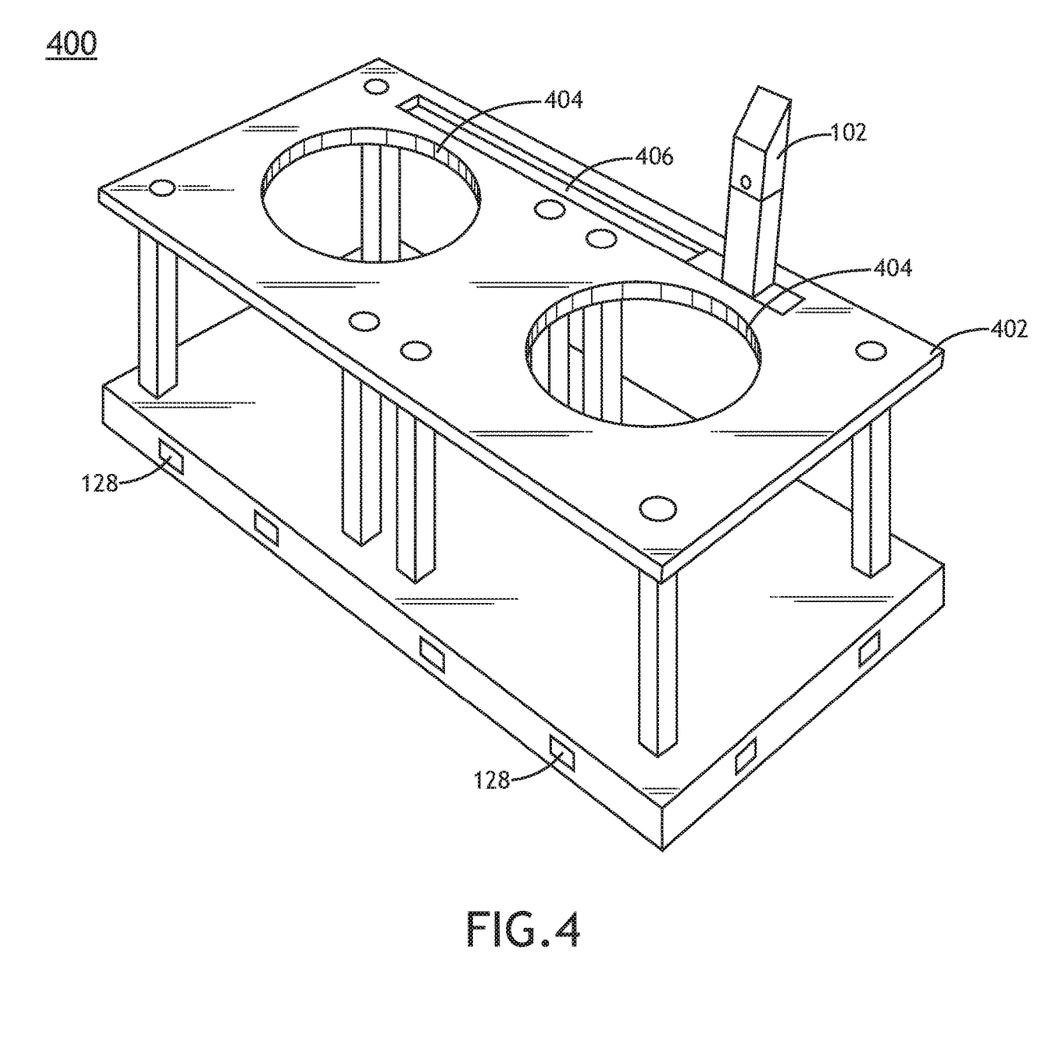
FIG. 4 illustrates an isometric view of a container holder able to hold a plurality of containers, in accordance with one or more embodiments of the present disclosure.

FIG. 4 depicts a container holder 400 configured to receive a plurality of specimen containers, in accordance with one or more embodiments of the present disclosure. In some embodiments, the container holder 400 is configured to receive a plurality of specimen containers (e.g., specimen containers 108). In this regard, the container holder 400 may include a first plate 402 with a plurality of container receiver openings defined by a plurality of inner surfaces 404. The discussion related to inner surface 106 of container holder 100 should be interpreted to extend to the plurality of inner surfaces 404 of container holder 400. The use of the plurality of inner surfaces 404 may allow for the container holder 400 to receive a plurality of specimen containers.

In some embodiments, the needle guide 102 (e.g., removable tip 120 or removable tip attachment point 118) may be attached to a slot 406 on the first plate (e.g., first plate 104, 204, 402). The slot 406 may be formed on the first plate and may include a recess to receive the needle guide 102. The slot 406 may allow the needle guide 102 to translate (e.g., slide) along the first plate between one or more inner surfaces and/or one or more depressions. In this regard, one needle guide may be used to retain a needle when draining liquid from the needle to a plurality of specimen containers and/or slides.

Figure 5:
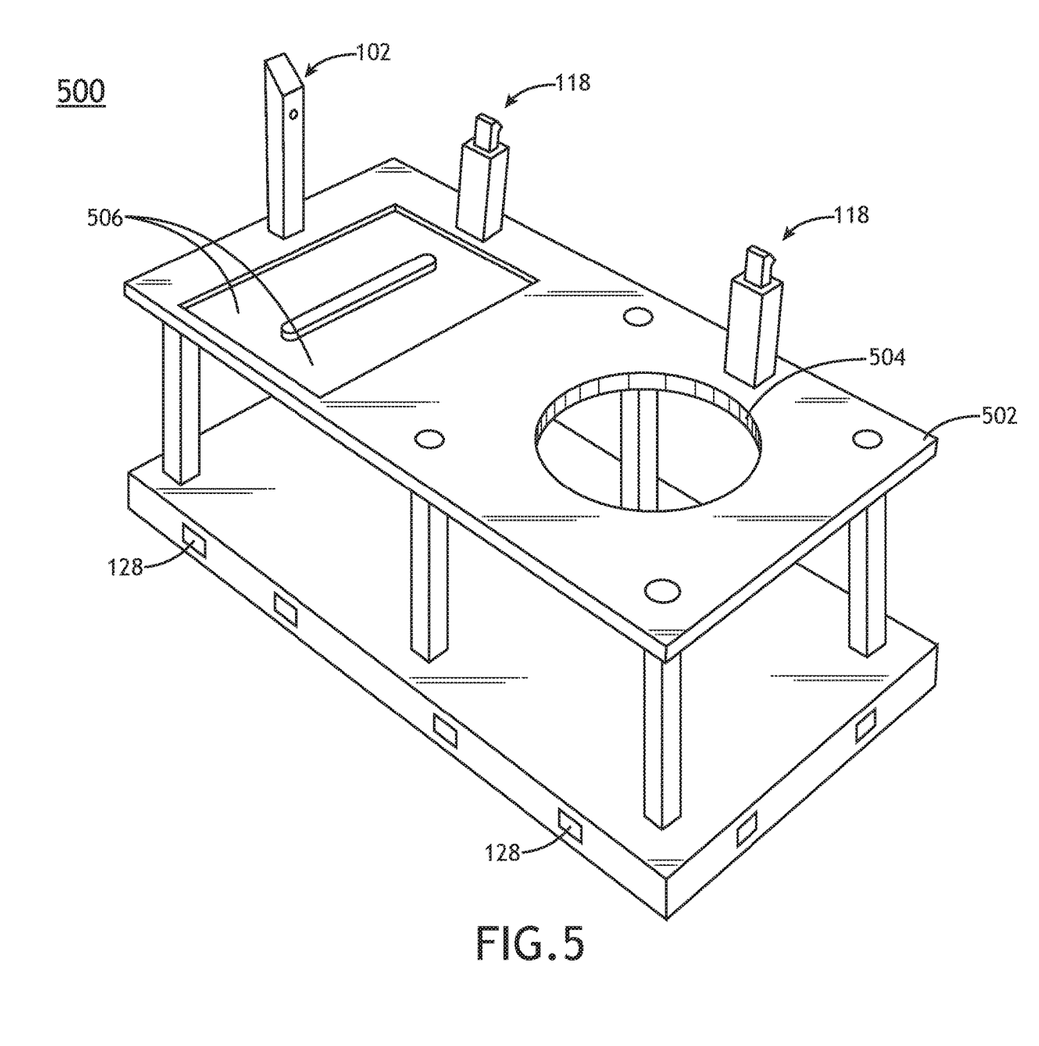
FIG. 5 illustrates an isometric view of an apparatus including a container holder and a slide holder, in accordance with one or more embodiments of the present disclosure.

FIG. 5 depicts an apparatus 500 including a slide holder and a container holder, in accordance with one or more embodiments of the present disclosure. In some embodiments, a first plate 502 of an apparatus 500 includes both container receiver opening defined by an inner surface 504 and one or more depressions 506. In this regard, the apparatus 500 may be configured to receive a specimen container by way of the inner surface 504 and may be configured to receive one or more slides by way of the one or more depressions 506 (e.g., depressions 202). The use of the first plate 502 including both the inner surface 504 and the one or more depressions 506 may provide several benefits, such as, but not limited to, reducing assembly time and reducing a cost of manufacturing. The configuration depicted in FIG. 5 is not intended to be limiting on the scope of the present disclosure. In this regard, the first plate 502 may include any number of inner surfaces 504 and depressions 506. Similarly, the first plate 502 may include any number and configuration of needle guides 102, secondary plates 110, 210, and/or tertiary plates 126 as disclosed herein. Furthermore, the first plate 502 may be detachably connected to additional container holders (e.g., container holders 100, 300) and/or slide holders (e.g., slide holders 200), in accordance with one or more additional embodiments of the present disclosure. Furthermore, the first plate 502 may include one or needle guides 102 fixed to the first plate or connected to a slot (e.g., slot 406).

Figure 6:
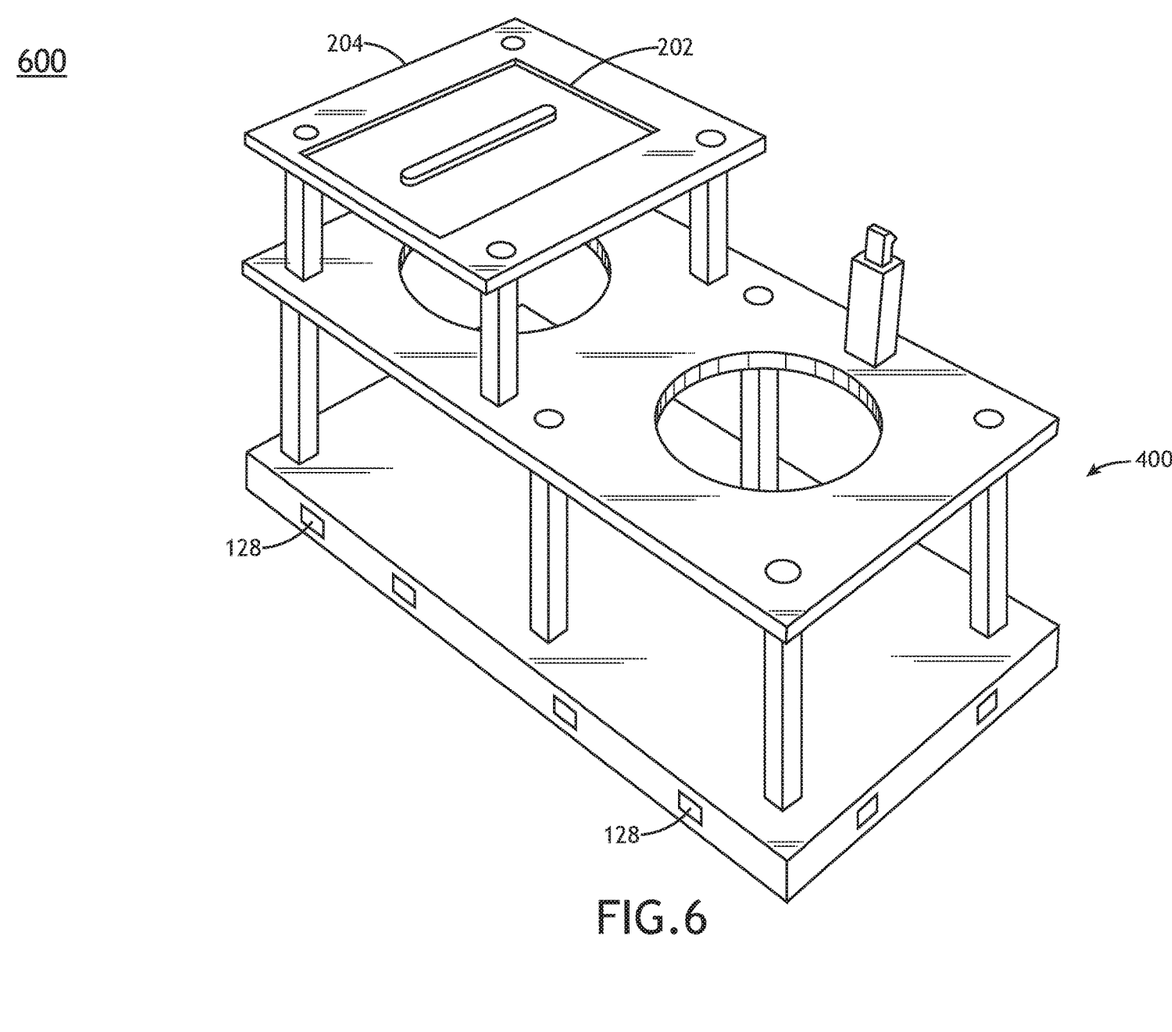
FIG. 6 illustrates an isometric view of an apparatus including a slide holder and a container holder, in accordance with one or more embodiments of the present disclosure.

FIG. 6 depicts an apparatus including a slide holder 602 stacked above a container holder, in accordance with one or more embodiments of the present disclosure. In some embodiments, one or more components of a slide holder (e.g., first plate 204) may be able to be stacked above a container holder (e.g., container holder 400, container holder 100, etc.) by one or more supports. The one or more supports may be attached (e.g., detachably or fixedly), in accordance with one or more embodiments of the present disclosure. The slide holder may be attached above the container holder by one or more holes (e.g., holes 114). The one or more holes may be the same as or in addition to the one or more holes used to connect the first plate to the second plate. In cases where the one or more holes are the same as those used to connect the first plate to the second plate, the one or more supports used to connect the first plate and the second plate may only fill up a portion of the holes in the first plate (e.g., a lower portion). In this regard, the supports used to connect the slide holder to the first plate may take up the remaining portion of the holes in the first plate (e.g., an upper portion).

Referring generally to FIGS. 1A-6, one or more of the inner surfaces 106, 404, 504, the depressions 202, 506, the supports 112, 212, the holes 114, or the means for detachably connecting the slide holders 200, the container holders 100, 300, 400, and/or the apparatus 500 may be pre-formed (e.g., during injection molding, additive manufacturing, etc.) or formed by a post-processing technique (e.g., CNC milling). Furthermore, such components may be any suitable material, including, but not limited to, a thermoplastic material (e.g., polycarbonate).

It is to be understood that the use of a container holder may increase the stability of a specimen container. Increased stability of the specimen container may be beneficial while performing a bronchoscopy, due to a reduced likelihood of tipping the specimen container over. The container holder may have increased stability due to a bottom portion of the container holder (e.g., second plate 110) being larger than a bottom of the specimen container. To further improve the stability of the specimen container, one or more components of the container holder (e.g., second plate 110) may be weighted (e.g., formed with additional material, formed of denser material, or including a secondary weight attached to the second plate 110). In this regard, the center of mass of the container holder may be shifted vertically towards the ground, reducing a likelihood of tipping. A slide holder may be similarly weighted.

The size of the container holder depicted in the figures of the present disclosure is not to be regarded as a limitation of the present disclosure. For example, the container holder may be configured to hold specimen containers of different sizes, such as, but not limited to, 1.5 ounces, 4 ounces, 8 ounces, 16 ounces, 32 ounces, 68 ounces, 165 ounces, etc. In this regard, a diameter of the container receiver opening defined by the inner surface of the first plate and a distance between the first plate and the second plate may be selected based on the size of the specimen container to be retained.

In some embodiments, one or more of the components described above (e.g., container holder, slide holder, needle guide, etc.) may come in a kit. In this regard, the one or more components may require assembly at or before the time of use. It is envisioned that such a kit may provide a user with increased flexibility based on a required use case. In some instances, the kit may be disassembled for cleaning. In other instances, only a portion of the kit is able to be disassembled easily (e.g., removable tip 120).

In some embodiments, a distance between a first plate and a second plate of a container holder may be less than the height of a specimen container. In this regard, the specimen container may be received by the container receiver opening of the first plate and sit on a top face of the second plate. In some instances, the specimen container may include a lid, which may be disposed above the first plate. In this regard, the specimen container may be configured to be held by the specimen holder, filled with specimen, and have the lid attached to the specimen container without removing the specimen container from the container holder, effectively reducing a likelihood of spilling the specimen.

The previous description is presented to enable one of ordinary skill in the art to make and use the invention as provided in the context of a particular application and its requirements. As used herein, directional terms such as "top," "bottom," "over," "under," "upper," "upward," "lower," "down," and "downward" are intended to provide relative positions for purposes of description, and are not intended to designate an absolute frame of reference. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

Although particular embodiments of this invention have been illustrated, it is apparent that various modifications and embodiments of the invention may be made by those skilled in the art without departing from the scope and spirit of the foregoing disclosure. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

What is claimed:

1. An apparatus comprising:
    a container holder including:
        a first plate with a container receiver opening defined by an inner surface configured to receive a specimen container;
        a needle guide attached to the first plate, the needle guide including a first and a second opening;
        wherein the needle guide is configured to receive a needle of a bronchoscope through the first and the second opening for draining a liquid from the bronchoscope through the needle to the specimen container; and
        a slide holder with one or more depressions configured to receive one or more slides, wherein the slide holder is detachably connected to the first plate.

2. The apparatus of claim 1, wherein the container holder further comprises:
    a second plate disposed below the first plate; and
    a plurality of supports disposed between the first plate and the second plate.

3. The apparatus of claim 2, wherein the container holder further comprises one or more intermediate plates disposed between the first plate and the second plate.

4. The apparatus of claim 2, wherein the first plate and the second plate are detachably connected by the plurality of supports.

5. The apparatus of claim 1, further comprising an additional container holder configured to detachably attach to the container holder.

6. The apparatus of claim 1, wherein the first plate of the container holder includes an additional container receiver opening defined by an additional inner surface configured to receive an additional specimen container.

7. The apparatus of claim 1, wherein the needle guide comprises a removable tip.

8. The apparatus of claim 7, where the removable tip of the needle guide includes the first opening and the second opening.

9. The apparatus of claim 1, further comprising at least one needle guide for the one or more depressions of the slide holder.

10. The apparatus of claim 1, wherein the slide holder is disposed on the first plate of the container holder.

11. The apparatus of claim 10, wherein the needle guide is slidable by a slot on the first plate.

12. The apparatus of claim 1, wherein the first opening of the needle guide has a first diameter and the second opening of the needle guide has a second diameter; wherein the first diameter is larger than the second diameter; wherein the first opening tapers towards the second opening through the needle guide.

13. A slide holder comprising:
    a first plate with one or more depressions, wherein each of the one or more depressions are configured to receive one or more slides; and
    a needle guide attached to the first plate, the needle guide including a first and a second opening;
    wherein the needle guide is configured to receive a needle of a bronchoscope through the first and the second opening for draining a liquid from the bronchoscope through the needle to the one or more slides, wherein the needle guide is slidable by a slot on the first plate.

14. The slide holder of claim 13, wherein the needle guide comprises a removable tip, wherein the removable tip of the needle guide includes the first opening and the second opening.

15. The slide holder of claim 13, further comprising:
    a second plate; and
    a plurality of supports disposed between the first plate and the second plate.

16. The slide holder of claim 15, wherein the first plate and the second plate are configured to be detachably connected by the plurality of supports.

17. The slide holder of claim 13, wherein the first opening of the needle guide has a first diameter and the second opening of the needle guide has a second diameter; wherein the first diameter is larger than the second diameter; wherein the first opening tapers towards the second opening through the needle guide.

* * * * *